(12) United States Patent
Elmandjra et al.

(10) Patent No.: US 7,247,142 B1
(45) Date of Patent: Jul. 24, 2007

(54) DIAGNOSIS OF PERIPHERAL VASCULAR DISEASE USING OXYGEN SATURATION

(75) Inventors: Mohamed Elmandjra, Pleasanton, CA (US); William O'Keefe, New Braunfels, TX (US); Jian Min Mao, Hayward, CA (US); Robin Bush, Newark, CA (US); Linda Christenson, Oakland, CA (US)

(73) Assignee: ViOptix, Inc., Fremont, CA (US)

( * ) Notice: Subject to any disclaimer, the term of this patent is extended or adjusted under 35 U.S.C. 154(b) by 486 days.

(21) Appl. No.: 10/838,142

(22) Filed: May 3, 2004

Related U.S. Application Data

(60) Provisional application No. 60/468,003, filed on May 5, 2003.

(51) Int. Cl.
*A61B 5/00* (2006.01)
*A61B 5/02* (2006.01)

(52) U.S. Cl. .............. 600/481; 600/500; 600/323
(58) Field of Classification Search .............. None
See application file for complete search history.

(56) References Cited

U.S. PATENT DOCUMENTS

2003/0236452 A1 * 12/2003 Melker et al. .......... 600/323

* cited by examiner

*Primary Examiner*—Robert L. Nasser
(74) *Attorney, Agent, or Firm*—Aka Chan LLP

(57) ABSTRACT

Techniques for diagnosing peripheral vascular disease using oxygen saturation are provided. Changes in oxygen saturation in tissue during recovery from induced ischemia are measured. The changes are then utilized to diagnose whether a patient has peripheral vascular disease.

16 Claims, 12 Drawing Sheets

StO2 Recovery Rate

| PTS Result | PVD status | |
| --- | --- | --- |
| | Positive | Negative |
| Positive | a = 10 (true positive) | b = 1 (false positive) |
| Negative | c = 0 (false negative) | d = 8 (true negative) |
| Sensitivity = a/(a+c) | 100% ± 0% ||
| Specificity = d/(b+d) | 89% ± 7% ||
| PPV = a/(a+b) | 91% ± 7% ||
| NPV = d/(c+d) | 100% ± 0% ||

*FIG. 7*

Recovery to 80%

| PTS Result | PVD status | |
|---|---|---|
| | Positive | Negative |
| Positive | a = 8 (true positive) | b = 0 (false positive) |
| Negative | c = 2 (false negative) | d = 9 (true negative) |
| Sensitivity = a/(a+c) | 80% ± 0% ||
| Specificity = d/(b+d) | 100% ± 7% ||
| PPV = a/(a+b) | 100% ± 7% ||
| NPV = d/(c+d) | 82% ± 0% ||

*FIG. 11*

DIAGNOSIS OF PERIPHERAL VASCULAR DISEASE USING OXYGEN SATURATION

This is a non-provisional of U.S. Application No. 60/468,003, filed May 5, 2003, which is hereby incorporated by reference for all purposes.

BACKGROUND OF THE INVENTION

The present invention relates to methods of diagnosing peripheral vascular disease (PVD) using measured changes in oxygen saturation in tissue. More specifically, the invention relates to diagnosing PVD from an analysis of oxygen saturation during recovery from ischemia (reduced or stoppage of blood flow).

Peripheral vascular disease is a condition that is exemplified by a narrowing of blood vessels to internal organs and muscles. Patients with PVD are four times more likely to have a myocardial infarction and three times more likely to have a stroke. The five year mortality rate for people with PVD is 30%. PVD affects 20% of the elderly and 40% of diabetics.

Unfortunately, it has been estimated that 8–12 million people in the United States are affected with this disease and the numbers are growing at a rate of 5% a year. Although these numbers show that PVD is a fairly common disease, PVD is often not diagnosed or is misdiagnosed. It has been estimated that 71% of physicians overlook a PVD condition in their patients.

It would be beneficial to have innovative techniques for diagnosing PVD. Additionally, it would be beneficial to have techniques of diagnosing PVD with relatively high accuracy rates.

SUMMARY OF THE INVENTION

The present invention provides innovative techniques for diagnosing peripheral vascular disease. In general, oxygen saturation in tissue of a patient is monitored during recovery from ischemia. For example, blood flow to a limb can be reduced or stopped utilizing a pressure cuff. When the cuff pressure is released, the oxygen saturation of the limb can be continuously monitored. The changes in oxygen saturation during the recovery from ischemia are then used to diagnose whether the patient has PVD. In this manner, not only can PVD be readily diagnosed, the accuracy of the diagnoses can be relatively high. Some specific embodiments of the invention are described below.

In one embodiment, the invention provides a method of diagnosing peripheral vascular disease. Oxygen saturation in tissue of a patient is measured during recovery from ischemia. The oxygen saturation in the tissue during the recovery is then analyzed. The patient is diagnosed as having peripheral vascular disease according to changes in the oxygen saturation in the tissue during the recovery. In some embodiments, the changes can be a rate of change of oxygen saturation and/or a time for oxygen saturation to recover a specific percentage.

In another embodiment, the invention provides a method of diagnosing peripheral vascular disease. Oxygen saturation in tissue of a patient is measured during recovery from ischemia. A rate of change of oxygen saturation during the recovery is calculated. The patient diagnosed as having peripheral vascular disease if the rate of change crosses a threshold. In some embodiments, the rate of change can be calculated at a mid-point of the recovery.

In another embodiment, the invention provides a method of diagnosing peripheral vascular disease. Oxygen saturation in tissue of a patient is measured during recovery from ischemia. A time for oxygen saturation to recover a specified percentage during the recovery is calculated. The patient is diagnosed as having peripheral vascular disease if the time for oxygen saturation to recover crosses a threshold. In some embodiments, the specified percentage is approximately 80%.

Other features and advantages of the invention will become readily apparent upon review of the following description in association with the accompanying drawings, where the same or similar structures are designated with the same reference numerals.

BRIEF DESCRIPTION OF THE DRAWINGS

FIG. 7 shows results of diagnoses of patients for PVD utilizing the rate of recovery of oxygen saturation.

FIG. 11 shows results of diagnoses of patients for PVD utilizing the time oxygen saturation to recover a specified percentage.

DETAILED DESCRIPTION OF PREFERRED EMBODIMENTS

In the description that follows, the present invention will be described in reference to embodiments that diagnose PVD utilizing changes in oxygen saturation in tissue during recovery from ischemia. However, embodiments of the invention are not limited to any particular environment, application or implementation. For example, although different techniques of monitoring changes in oxygen saturation will be described, the invention is not limited to the specific embodiments described below. Therefore, the description of the embodiments that follows is for purposes of illustration and not limitation.

Figure 1:
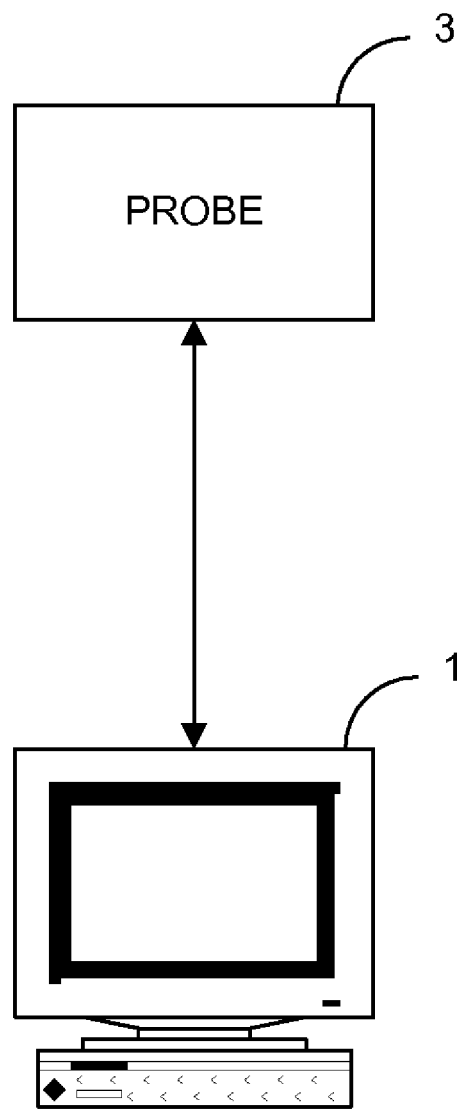
FIG. 1 shows an example of a computer system and probe for measuring oxygen saturation in tissue.

FIG. 1 shows an example of a system for diagnosing PVD. A computer system 1 is connected to a probe 3. Probe 3 is typically placed in close contact to a patient's tissue in order to collect data that can be analyzed by computer system 1 in order to determine oxygen saturation in the tissue.

In some embodiments, the system for measuring oxygen saturation in tissue is as described in U.S. patent application Ser. No. 09/877,515, filed Jun. 7, 2001, which is hereby incorporated by reference for all purposes. For example, the oxygen saturation system can use continuous wave spectroscopy (CWS) to determine absolute values of concentrations of oxygenated and deoxygenated hemoglobins in a patient's tissue. In other embodiments, other systems for measuring oxygen saturation in tissue can be utilized.

Figure 2:
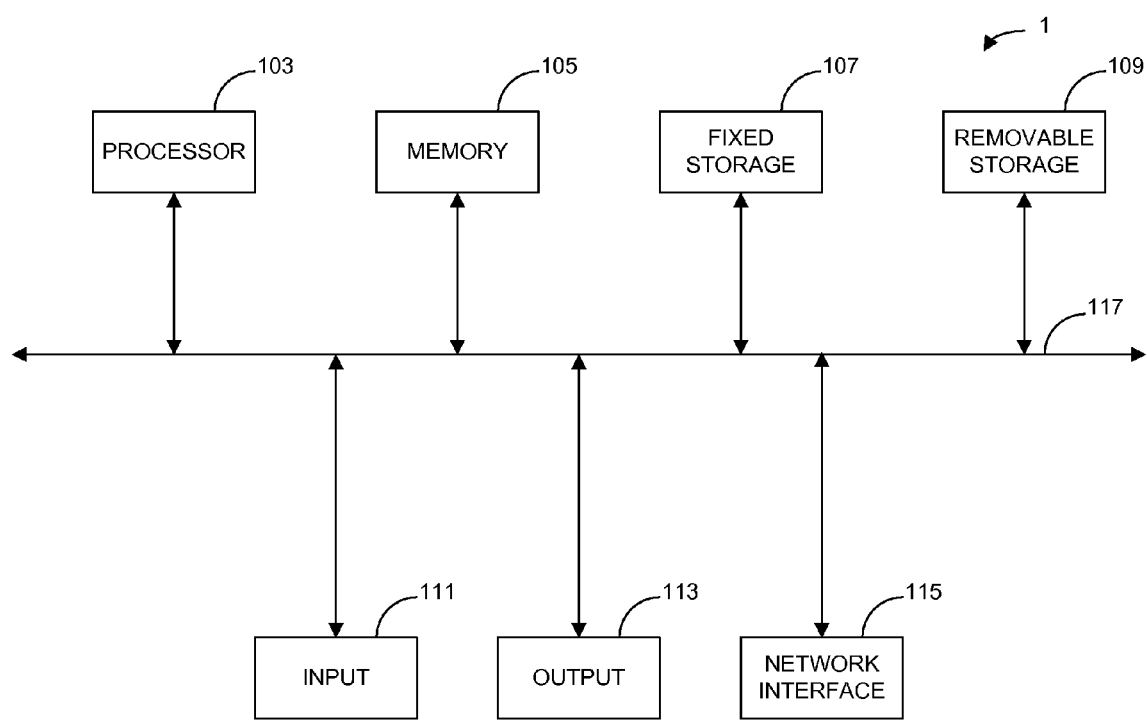
FIG. 2 illustrates a block diagram of a computer system that can be utilized in association with embodiments of the invention.

FIG. 2 shows a block diagram of components that can be present in computer systems that implement embodiments of the invention. A computer system 1 includes a processor 103 that executes instructions from computer programs (including operating systems). Although processors typically have memory caches also, processor 103 utilizes memory 105, which can store instructions or computer code and data.

A fixed storage (e.g., hard drives or drives) 107 can store computer programs and data such that it is typically persistent and provides more storage when compared to memory 105. A removable storage 109 provides mobility to computer programs and/or data that are stored thereon. Examples of removable storage are floppy disks, tape, CD/ROM, flash memory devices, and the like.

Memory 103, fixed storage 107 and removable storage 109 provide examples of computer readable storage media that can be utilized to store and retrieve computer programs incorporating computer codes that implement the invention, data for use with the invention, and the like. Additionally, a data signal embodied in a carrier wave (e.g., in a network including the Internet) can be the computer readable storage medium. An input 111 allows a user to interface with the system. Input can be done through the use of a keyboard, a mouse, buttons, dials, or any other input mechanism. An output 113 allows the system to provide output to the user. Output can be provided through a monitor, display screen, LEDs, printer or any other output mechanism.

A network interface 115 allows the system to interface with a network to which it is connected. The system bus architecture of computer system 101 is represented by arrows 117. The components shown in FIG. 2 can be found in many computer systems. However, components can be added, deleted and combined. Thus, FIG. 3 is for illustration purposes and not limitation.

Figure 3:
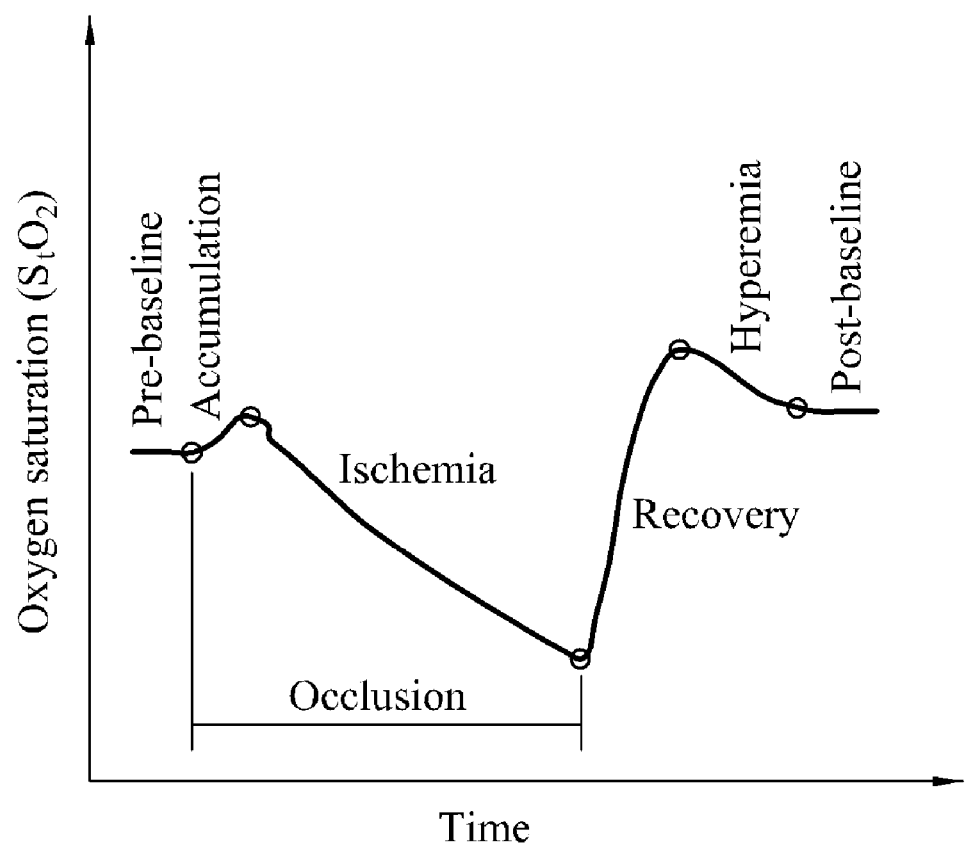
FIG. 3 shows a graph of oxygen saturation over time through induced ischemia and subsequent recovery.

FIG. 3 shows a graph of oxygen saturation through induced ischemia and subsequent recovery. The measurements were obtained as follows.

A subject was laying supine in a resting state. Sensors were positioned over the anterior tibialis muscle flat against the skin with minimal coupling pressure. Initial oxygen saturation measurements were then taken.

Occlusion of anterior blood flow to a lower limb was induced by inflating a cuff to 30 mmHg above systolic pressure. Cessation of blood flow was confirmed with a doppler. Occlusion was maintained for five minutes and then the occlusion was removed so that blood flow was rapidly restored. During this time, oxygen saturation was continuously monitored and recorded as indicated in the graph.

The graph in FIG. 3 can be broken into many different phases as shown. A pre-baseline phase is where the cuff was not inflated and the subject was at rest. This stage shows the oxygen saturation level as a baseline before occlusion.

An accumulation phase is at the beginning of occlusion immediately following the cuff inflation, which causes oxyhemoglobin accumulation in the tissue.

An ischemic phase is the period following the accumulation phase while the cuff remain inflated and oxygen was being consumed. As shown, oxygen saturation steadily declines during this phase.

A recovery phase is the beginning post occlusive period, immediately following the cuff deflation, while fresh arterial blood is returning and oxygen saturation increase rapidly. As shown, oxygen saturation rose higher than the pre baseline oxygen saturation (called "overshooting").

A hyperemia phase was the post occlusive reactive hyperemic (PORH). While oxygen saturation decreased from its peak due to overshooting and reaches the post occlusive baseline phase.

Figure 4:
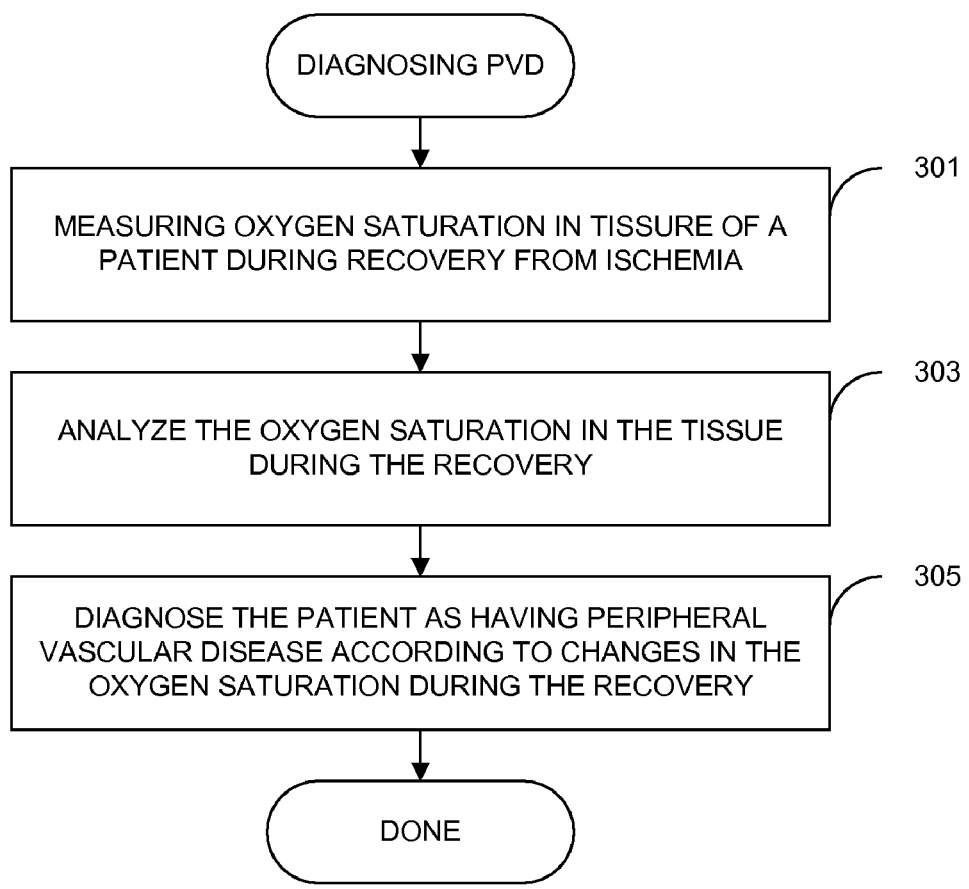
FIG. 4 shows a flow chart of a process of diagnosing PVD according to one embodiment of the invention.

Embodiments of the invention utilize changes in oxygen saturation during recovery from induced ischemia to diagnose PVD. FIG. 4 shows a flowchart of a process of diagnosing PVD utilizing changes in oxygen saturation during the recovery.

At step 301, oxygen saturation in tissue of a patient during recovery from ischemia is measured. The oxygen saturation in the tissue during the recovery is analyzed at a step 303.

At a step 305, the patient is diagnosed as having peripheral vascular disease according to changes in the oxygen saturation during the recovery. The changes in oxygen saturation can be measured in various ways.

Figure 5:
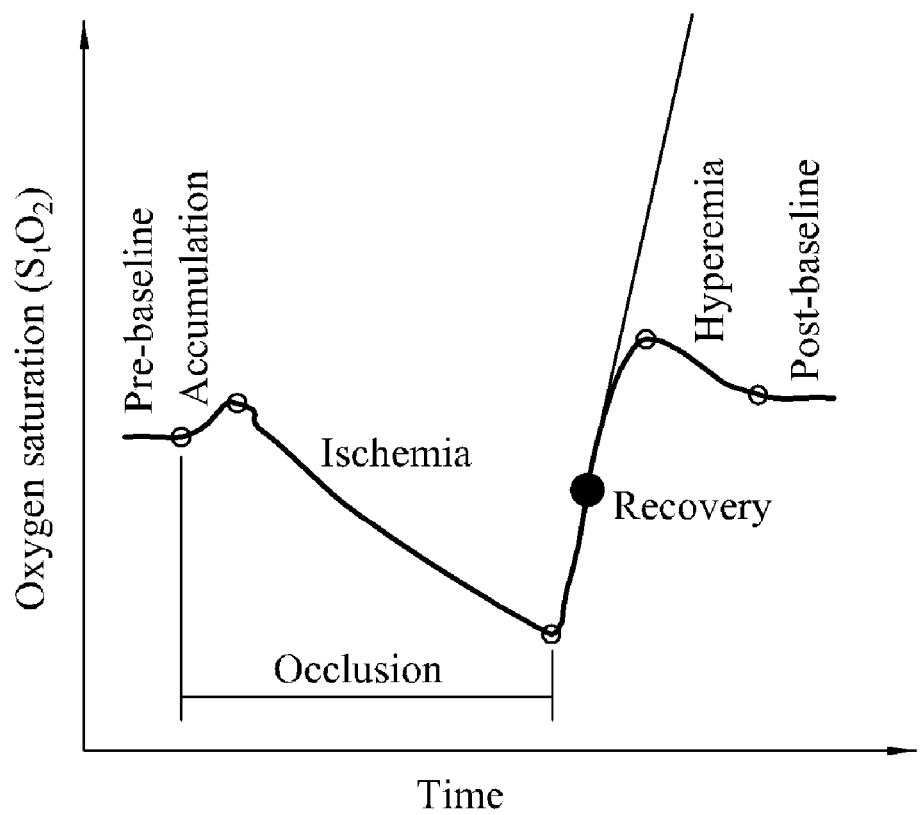
FIG. 5 shows a graph including the rate of change of oxygen saturation during recovery from ischemia.

In one embodiment, the changes in oxygen saturation are measured by the rate of change of oxygen saturation during recovery from ischemia. FIG. 5 shows a graph of the rate of recovery of oxygen saturation during recovery. As shown, the rate of change is measured at a mid-point in the recovery phase.

Figure 6:
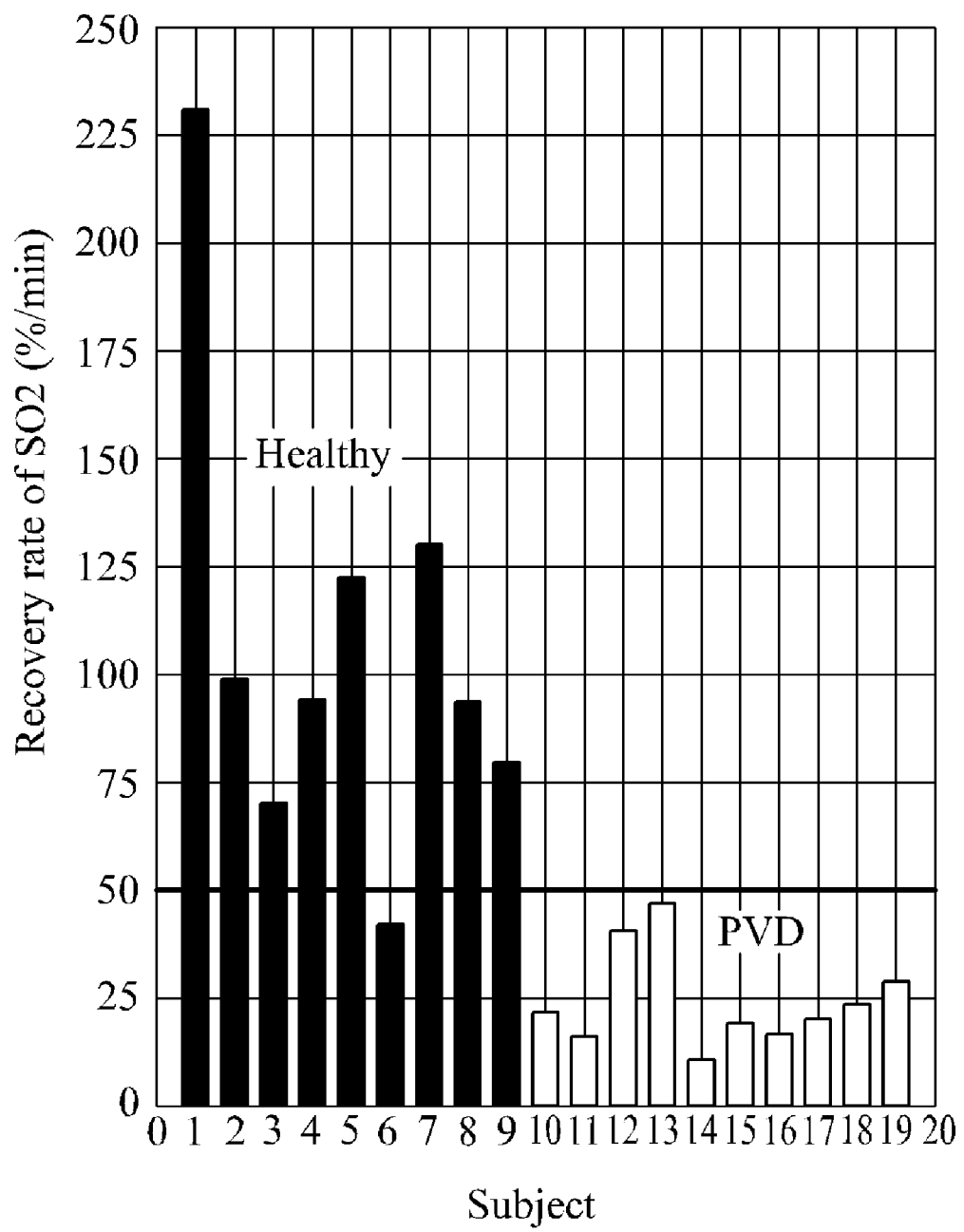
FIG. 6 shows a bar graph of various patients and diagnoses of PVD utilizing the rate of recovery of oxygen saturation.

FIG. 6 shows a bar graph of the rate of change of oxygen saturation during recovery for various patients. As shown, healthy patients have typically a higher rate of change of oxygen saturation during recovery. According a diagnosis of PVD can be made based on whether the rate of change oxygen saturation crosses a threshold (in this case is below a threshold), such as is shown in FIG. 6.

FIG. 7 shows results utilizing this technique for diagnosing PVD. As shown, there were ten true positives, eight true negatives, no false negatives and only one false positive.

Figure 8:
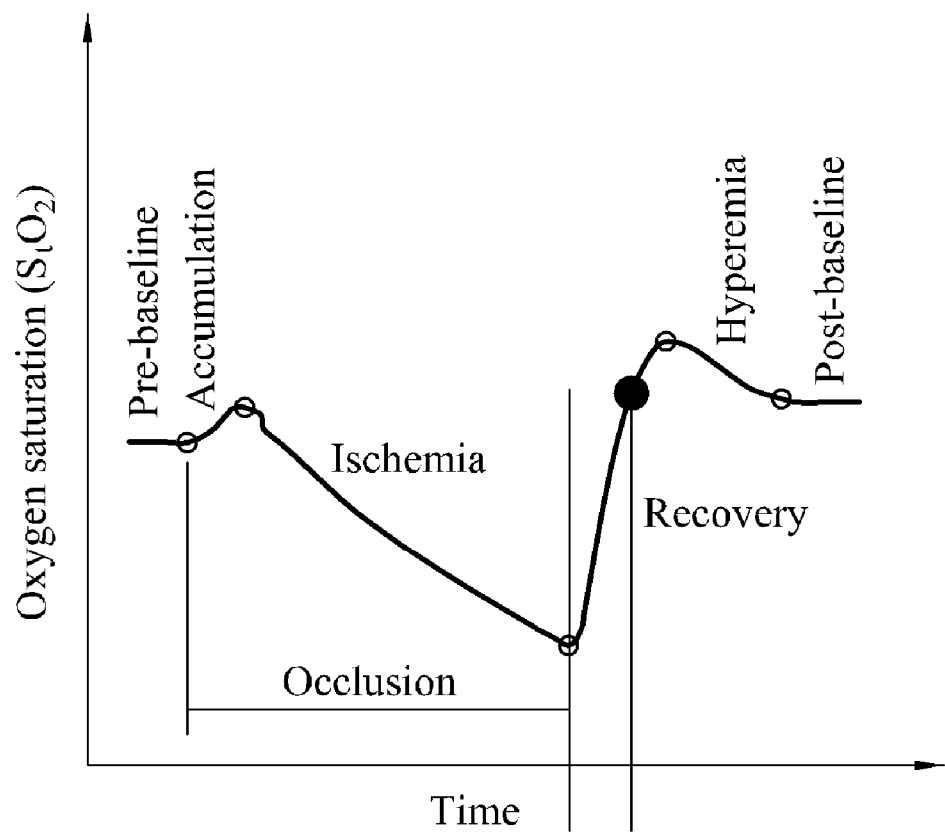
FIG. 8 shows a graph including the time for oxygen saturation to recover to a specified percentage during recovery from ischemia.

In another embodiment, the change in oxygen saturation during recovery is measured by the time for oxygen saturation to recover a specified percentage. FIG. 8 shows a graph of the time needed for oxygen saturation to recover 80% of the oxygen saturation through the recovery phase.

Figure 9:
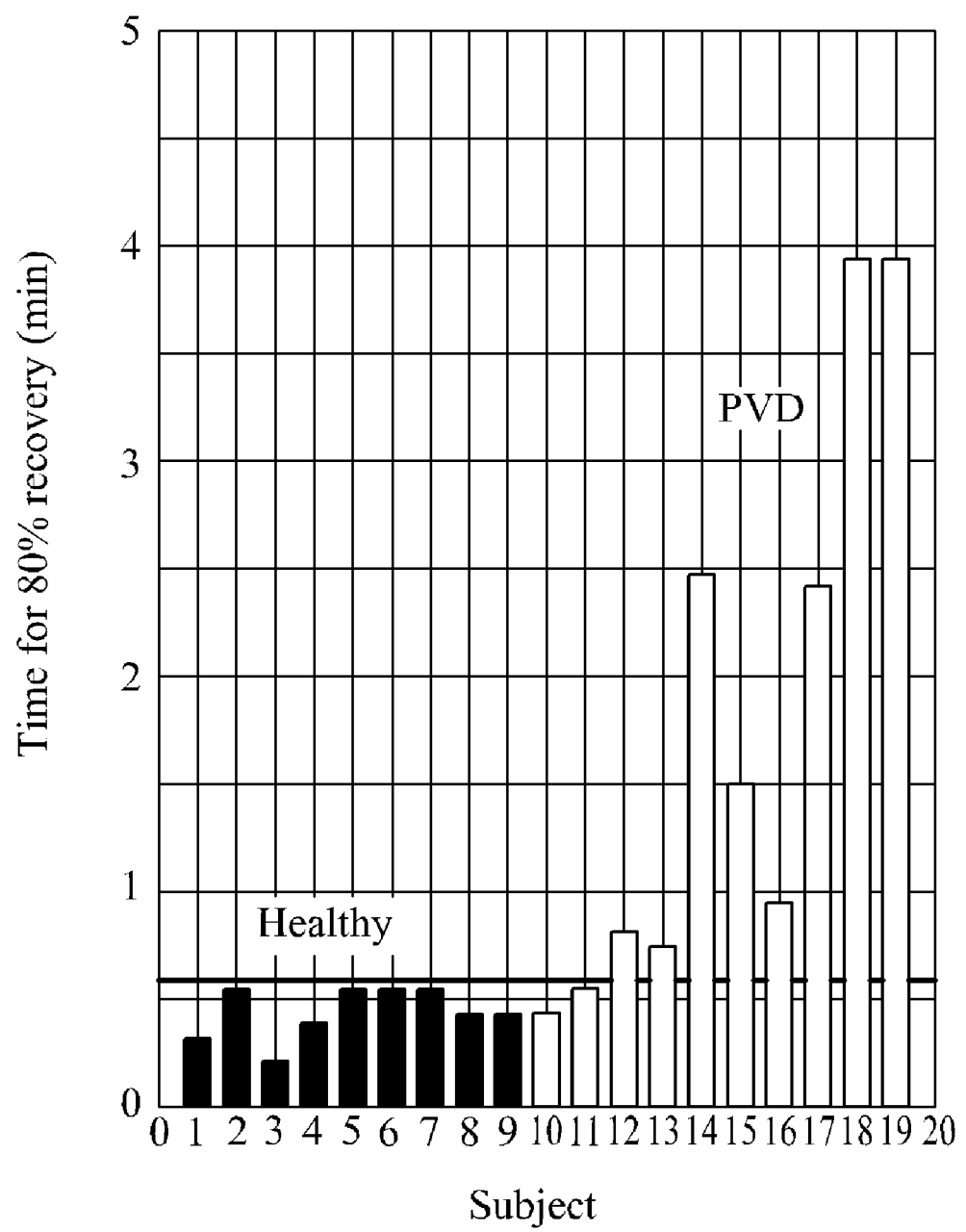
FIG. 9 shows a bar graph of various patients and the diagnoses of PVD utilizing the time for oxygen saturation to recover a specified percentage.

FIG. 9 shows a bar graph of the time for oxygen saturation to recover to a specified percentage during recovery for various individuals. As shown, patients with PVD demonstrated more time was taken to recover oxygen saturation to 80%. Accordingly, PVD can be diagnosed according to whether the time for oxygen saturation to recover a specified percentage crosses a threshold (in this case is above a threshold) as shown in FIG. 9.

Figure 10:
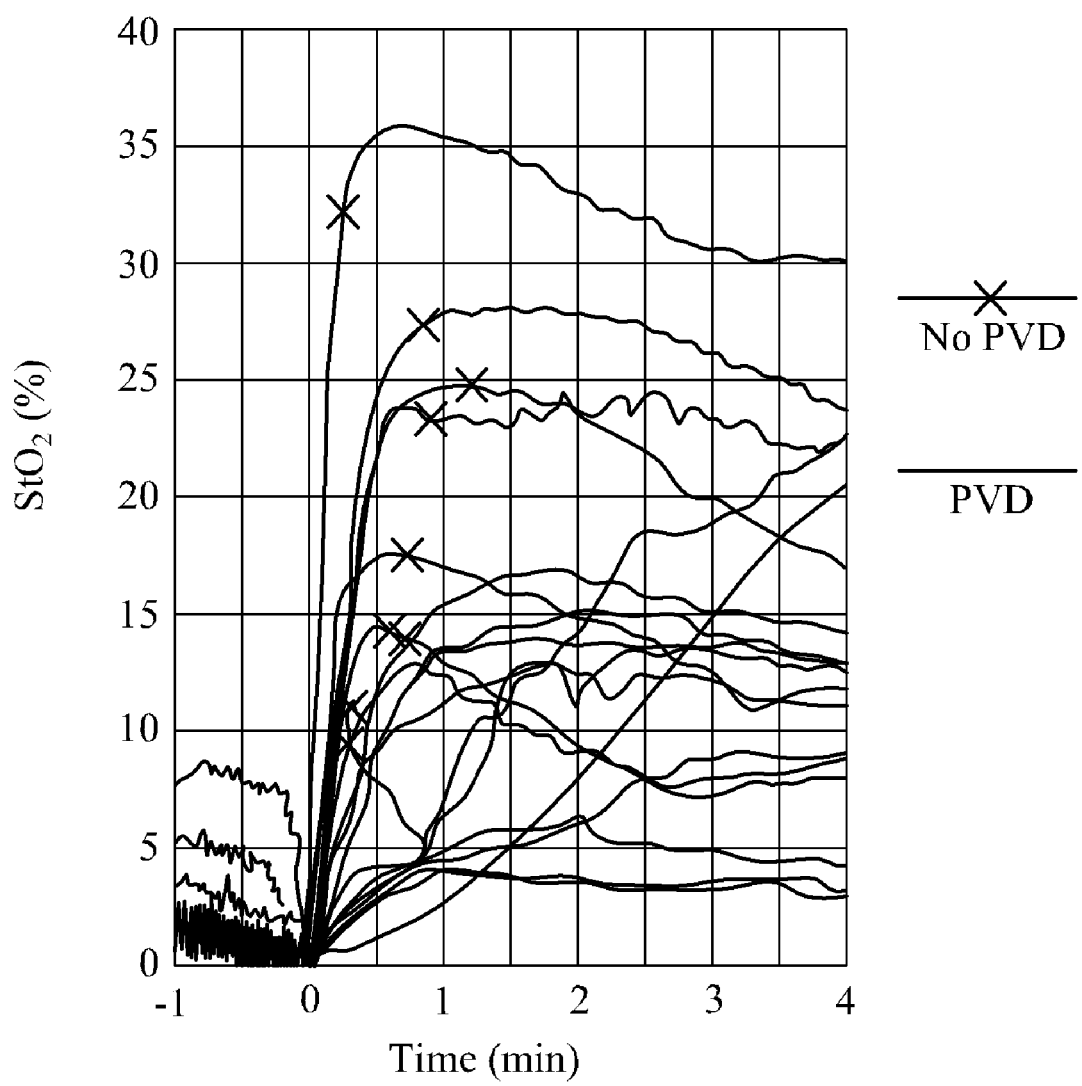
FIG. 10 shows a graph of patients and their oxygen saturation recovery over time.
Figure 12:
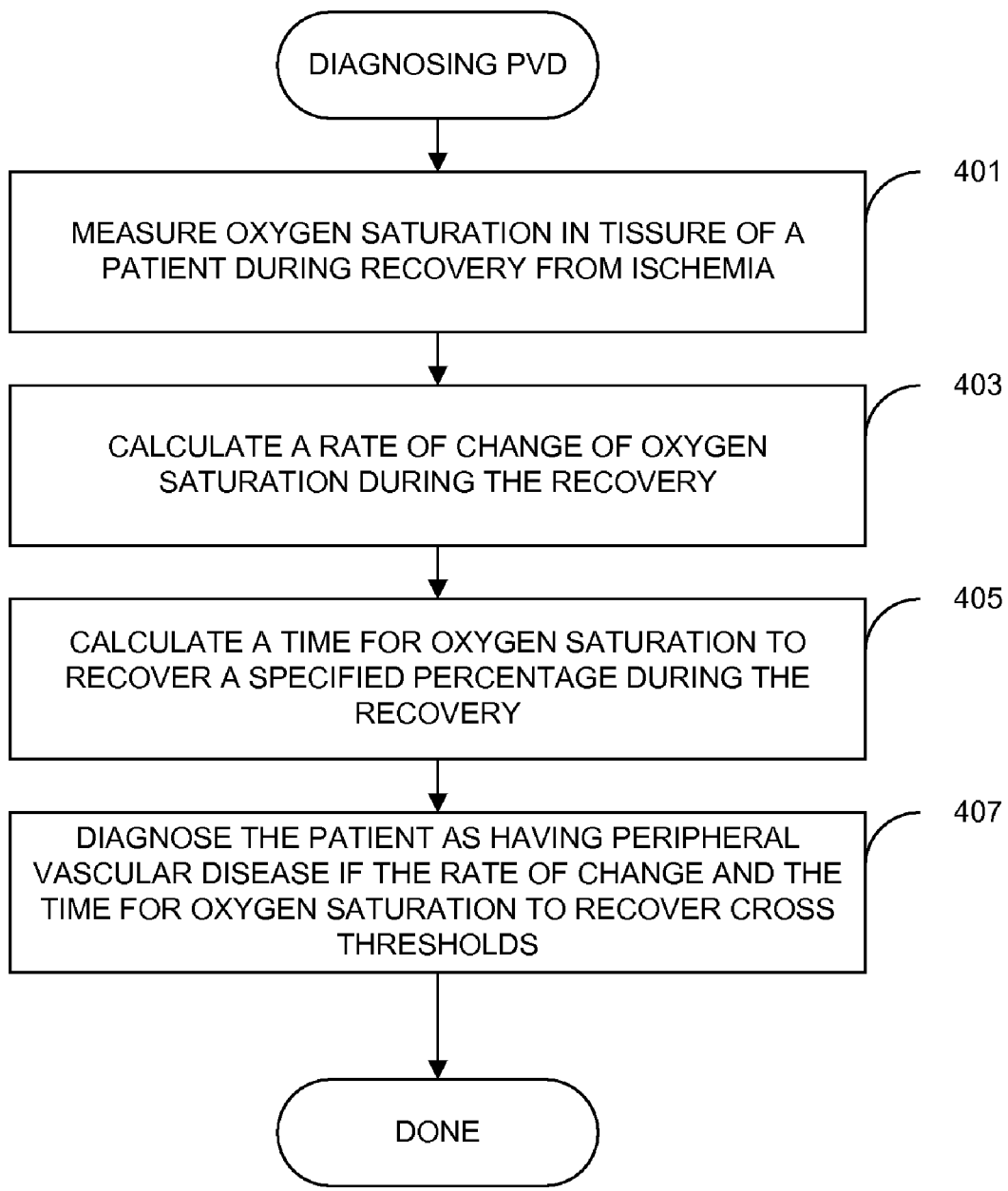
FIG. 12 shows a flow chart of another process of diagnosing PVD according to the invention.

FIG. 10 shows a graph of the oxygen saturation in tissue of patients over time for patients without PVD and with PVD. As shown, patients without PVD typically recover oxygen saturation more quickly than patients with PVD.

FIG. 11 shows results from varies patients utilizing this technique for diagnosing PVD. As shown, there were eight true positives, nine true negative, zero false positives and only two false negatives.

Although the preceding has described different methods for measuring changes in oxygen saturation during recovery, the invention can utilize any methods of measuring any changes oxygen saturation. Additionally, one or more different methods of measuring changes in oxygen saturation during recovery can be combined in order to provide diagnoses for PVD.

FIG. 11 shows a flow chart of another process of diagnosing PVD. At a step 401, oxygen saturation in tissue of a patient during recovery from ischemia is measured. A rate of change of oxygen saturation during the recovery is calculated at a step 403. The rate of change can be calculated as described previously. At a step 405, a time for oxygen saturation to recover a specified percentage during the recovery is calculated. The time can be calculated as discussed previously.

At a step 407, the patient can be diagnosed as having peripheral vascular disease if the rate of change and the time for oxygen saturation to recover cross thresholds. By utilizing multiple methods of measuring changes in oxygen saturation during recovery, greater accuracy in diagnosing PVD can be obtained.

While the above is a complete description of preferred embodiments of the invention, various alternatives, modifications, and equivalents can be used. It should be evident that the invention is equally applicable by making appropriate modifications to the embodiments described above. Therefore, the above description should not be taken as limiting the scope of the invention that is defined by the metes and bounds of the appended claims along with their full scope of equivalents.

What is claimed is:

1. A method of diagnosing peripheral vascular disease, comprising:
   measuring oxygen saturation in tissue of a patient during recovery from ischemia;
   analyzing the oxygen saturation in the tissue during the recovery; and
   diagnosing the patient as having peripheral vascular disease according to changes in the oxygen saturation in the tissue during the recovery.

2. The method of claim 1, wherein the analyzing the oxygen saturation comprises calculating a rate of change of oxygen saturation during the recovery.

3. The method of claim 2, wherein the rate of change is calculated at a mid-point of the recovery.

4. The method of claim 2, wherein the diagnosing the patient comprises determining if the rate of change crosses a threshold.

5. The method of claim 1, wherein the analyzing the oxygen saturation comprises calculating a time for oxygen saturation to recover a specified percentage during the recovery.

6. The method of claim 5, wherein the specified percentage is approximately 80%.

7. The method of claim 5, wherein the diagnosing the patient comprises determining if the time for oxygen saturation to recover crosses a threshold.

8. The method of claim 1, wherein the analyzing the oxygen saturation comprises:
   calculating a rate of change of oxygen saturation during the recovery; and
   calculating a time for oxygen saturation to recover a specified percentage during the recovery.

9. The method of claim 8, wherein the diagnosing the patient comprises determining if the rate of change and the time for oxygen saturation to recover cross thresholds.

10. An apparatus for diagnosing peripheral vascular disease, comprising:
    a device to cause ischemia in tissue
    a probe that measures oxygen saturation in the tissue of a patient during recovery from induced ischemia;
    a computer, coupled to the probe, that analyzes the oxygen saturation in the tissue during the recovery and diagnoses the patient as having peripheral vascular disease according to the oxygen saturation in the tissue during the recovery.

11. A method of diagnosing peripheral vascular disease, comprising:
    measuring oxygen saturation in tissue of a patient during recovery from ischemia;
    calculating a rate of change of oxygen saturation during the recovery; and
    diagnosing the patient as having peripheral vascular disease if the rate of change crosses a threshold.

12. The method of claim 11, wherein the rate of change is calculated at a mid-point of the recovery.

13. An apparatus for diagnosing peripheral vascular disease, comprising:
    a probe that measures oxygen saturation in tissue of a patient during recovery from ischemia;
    a computer, coupled to the probe, that calculates a rate of change of oxygen saturation during the recovery and diagnoses the patient as having peripheral vascular disease if the rate of change crosses a threshold.

14. A method of diagnosing peripheral vascular disease, comprising:
    measuring oxygen saturation in tissue of a patient during recovery from ischemia;
    calculating a time for oxygen saturation to recover a specified percentage during the recovery; and
    diagnosing the patient as having peripheral vascular disease if the time for oxygen saturation to recover crosses a threshold.

15. The method of claim 14, wherein the specified percentage is approximately 80%.

16. An apparatus for diagnosing peripheral vascular disease, comprising:
    a probe that measures oxygen saturation in tissue of a patient during recovery from ischemia;
    a computer, coupled to the probe, that calculates a time for oxygen saturation to recover a specified percentage during the recovery and diagnoses the patient as having peripheral vascular disease if the time for oxygen saturation to recover crosses a threshold.

* * * * *